(12) United States Patent
Kitching et al.

(10) Patent No.: US 10,258,439 B1
(45) Date of Patent: Apr. 16, 2019

(54) METHOD OF MANUFACTURING ORTHODONTIC DEVICES

(71) Applicant: Ormco Corporation, Orango, CA (US)

(72) Inventors: Ian D. Kitching, Highland, CA (US); Evan Yifeng Tsai, Pasadena, CA (US)

(73) Assignee: Ormco Corporation, Orange, CA (US)

( * ) Notice: Subject to any disclaimer, the term of this patent is extended or adjusted under 35 U.S.C. 154(b) by 483 days.

(21) Appl. No.: 14/947,315

(22) Filed: Nov. 20, 2015

Related U.S. Application Data

(60) Provisional application No. 62/082,428, filed on Nov. 20, 2014.

(51) Int. Cl.
*A61C 13/00* (2006.01)
*A61C 13/34* (2006.01)

(52) U.S. Cl.
CPC .......... *A61C 13/0004* (2013.01); *A61C 13/34* (2013.01); *Y10T 29/49568* (2015.01)

(58) Field of Classification Search
CPC . A61C 13/0004; A61C 13/34; A61C 13/0006; Y10T 29/49568; Y10T 29/49567
See application file for complete search history.

(56) References Cited

U.S. PATENT DOCUMENTS

| | | | | |
|---|---|---|---|---|
| 5,605,459 A | * | 2/1997 | Kuroda | A61C 7/002 433/214 |
| 8,545,221 B2 | | 10/2013 | Stone-Collonge et al. | |
| 8,573,972 B2 | | 11/2013 | Matov et al. | |
| 9,336,336 B2 | * | 5/2016 | Deichmann | A61C 13/0004 |

OTHER PUBLICATIONS

Pacquette, D.E., "Importance of the occlusal plane in virtual treatment planning," Journal of Clinical Orthodontics 45 (4), 217-221 (2011).

* cited by examiner

*Primary Examiner* — Sarang Afzali
(74) *Attorney, Agent, or Firm* — Wood Herron & Evans LLP

(57) ABSTRACT

A computational device determines a representation of one or more anatomical features, and based on the determined representation of the one or more anatomical features, a three-dimensional model is oriented in a three-dimensional space in an anatomically accurate manner. Thereafter, an orthodontic device design is created using the oriented three dimensional model and an orthodontic device is manufactured based at least in part on the orthodontic device design.

19 Claims, 21 Drawing Sheets

METHOD OF MANUFACTURING ORTHODONTIC DEVICES

1. FIELD

The disclosure relates to a system, method, and computer readable storage medium for orienting three-dimensional models in space in an anatomically accurate manner.

2. BACKGROUND

Orthodontics is a specialty of dentistry that is concerned with improvement of the general appearance of a patient's teeth and also the correction of malocclusions, crookedness and other flaws of the teeth. Orthodontic braces are devices that are placed on a patient's teeth by a dental practitioner. Often, such orthodontic braces are periodically adjusted by the dental practitioner to help align and straighten the teeth. Treatment by the dental practitioner may help in repositioning the teeth to correct flaws and improve the general appearance of the patient.

The dental practitioner may take impressions and capture X-ray images of the teeth and the surrounding skeletal structure. The X-ray images may be generated via digital radiography in which a digital image capture device is used for recording the X-ray images, and subsequently the X-ray images are saved as digital files. The X-ray images may include panoramic X-rays and cephalometric X-rays. The panoramic X-rays may show the relative positions of the teeth over the upper jaw and the lower jaw. The cephalometric X-rays may show the skeletal relationships associated with the teeth in different views of the head. Lateral cephalometric X-rays are in most cases taken from the right side of a patient's face. The cephalometric X-ray may also provide information about various angles and relationships associated with the teeth and the surrounding facial skeletal structure. Cephalometric analysis is the study of the dental and skeletal relationships in the head. Cephalometric software may be used to help calculate the angles and measurements for cephalometric analysis from the digital cephalometric X-rays.

Cone beam computed tomography (CBCT) involves the use of a rotating CBCT scanner, combined with a digital computer, to obtain images of the teeth and surrounding bone structure, soft tissue, muscle, blood vessels, etc. CBCT may be used in a dental practitioner's office to generate cross sectional images of teeth and the surrounding bone structure, soft tissue, muscle, blood vessels, etc. During a CBCT scan, the CBCT scanner rotates around the patient's head and may obtain hundreds of distinct CBCT images. The scanning software collects and analyzes the CBCT images to generate three-dimensional anatomical data. The three-dimensional anatomical data can then be manipulated and visualized with specialized software to allow for cephalometric analysis of the CBCT images.

Intra-oral imaging system is a diagnostic equipment that allows a dental practitioner to see the inside of a patient's mouth and display the topographical characteristics of teeth on a display monitor. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingivae.

A dental practitioner may write a prescription based on an analysis of the impression of the teeth, the X-ray images, the CBCT images, intra-oral imagery, etc. While performing the analysis the dental practitioner may use software for cephalometric analysis of the CBCT images, the panoramic X-rays, and the cephalometric X-rays. The prescription written by the dental practitioner may be used to manufacture an orthodontic brace or aligners. In a traditional orthodontic brace, wires interact with brackets to move teeth to a desired position. Periodic adjustments are needed to the orthodontic brace for satisfactory completion of treatment. Other methods that use clear removable plastic aligners that level and align teeth may also be used by certain dental practitioners.

As described above, digital imagery is widely used in dental diagnosis and treatment planning Three-dimensional models that represent teeth may be used for performing various operations related to dentistry, such as the design of braces or aligners. Such models of teeth may be manipulated within a three-dimensional graphics system for providing various types of display for use by a dental practitioner. The models may comprise three-dimensional digital representations of a patient's teeth and may be also referred to as virtual models (as opposed to physical models that may be cast in plaster). Software platforms may allow dental practitioners to modify virtual models (i.e., three-dimensional digital representations) of a patient's teeth, where the virtual models are suspended in space on display screens.

SUMMARY OF THE PREFERRED EMBODIMENTS

Provided are a method, a system, and a computer program product in which a computational device determines a representation of one or more anatomical features, and based on the determined representation of the one or more anatomical features, a three-dimensional model is oriented in a three-dimensional space in an anatomically accurate manner.

In additional embodiments, the three-dimensional model comprises a model for teeth.

In further embodiments, the representation of the one or more anatomical features comprises a Frankfort horizontal.

In yet further embodiments, the Frankfort horizontal is in a fixed relationship with an occlusal plane of the teeth and is parallel to a reference plane.

In additional embodiments, the reference plane is parallel to a floor. A horizontal line corresponding to the Frankfort horizontal is determined in a lateral cephalometric image that includes the teeth. The lateral cephalometric image is used to orient the three-dimensional model of the teeth in the three-dimensional space.

In further embodiments, determining the horizontal line corresponding to the Frankfort horizontal further comprises determining at least two different points on a line representing the Frankfort horizontal.

In additional embodiments, determining the horizontal line corresponding to the Frankfort horizontal further comprises identifying and displaying left to right straight lines in a cephalometric tracing of the cephalometric image, and determining which of the displayed left to right straight lines has been selected by a user as a line corresponding to the Frankfort horizontal.

In further embodiments, left to right straight lines are identified in a cephalometric tracing of the cephalometric image. A determination is made as to which of the left to right straight lines corresponds to the Frankfort horizontal.

In certain embodiments, using the lateral cephalometric image to orient a three-dimensional model of the teeth in three-dimensional space further comprises identifying and matching a silhouette of the teeth in the three-dimensional model of the teeth and the lateral cephalometric image.

In further embodiments, the silhouette of the teeth comprises an envelope of all incisal and buccal edges of teeth that are visible.

In yet further embodiments, rotations of the three-dimensional model are performed to further match the silhouette of the teeth in the three-dimensional model of the teeth and the lateral cephalometric image.

In additional embodiments, a frontal photograph with displayed teeth is used to orient the three-dimensional model of the teeth in the three-dimensional space.

In additional embodiments, rotational adjustments are made to the three-dimensional model of the teeth in three-dimensional space to orient the three-dimensional model of the teeth in the three-dimensional space.

In further embodiments, graphical user interface controls are used to position and orient the three-dimensional model of the teeth in the three-dimensional space.

In further embodiments, a method of manufacturing an orthodontic device is provided. The method comprises determining, by a computational device, a representation of one or more anatomical features and orienting, based at least in part on the determined representation of the one or more anatomical features, a three-dimensional model in a three-dimensional space in an anatomically accurate manner. The method further comprises creating, using the oriented three dimensional model, an orthodontic device design and manufacturing the orthodontic device based at least in part on the orthodontic device design.

In further embodiments, a system for manufacturing an orthodontic device is provided. The system comprises a memory and a processor coupled to the memory, wherein the processor performs operations. The operations comprise determining a representation of one or more anatomical features and orienting, based on the determined representation of the one or more anatomical features, a three-dimensional model in a three-dimensional space in an anatomically accurate manner. The operations further comprise creating, using the oriented three dimensional model, an orthodontic device design and manufacturing the orthodontic device based at least in part on the orthodontic device design.

In further embodiments, a computer readable storage medium is provided, wherein code stored in the computer readable storage medium when executed by a processor performs operations. The operations comprise determining a representation of one or more anatomical features and orienting, based on the determined representation of the one or more anatomical features, a three-dimensional model in a three-dimensional space in an anatomically accurate manner. The operations further comprise creating, using the oriented three dimensional model, an orthodontic device design and manufacturing an orthodontic device based at least in part on the orthodontic device design.

BRIEF DESCRIPTION OF THE DRAWINGS

Referring now to the drawings in which like reference numbers represent corresponding parts throughout.

DETAILED DESCRIPTION

Figure 1:
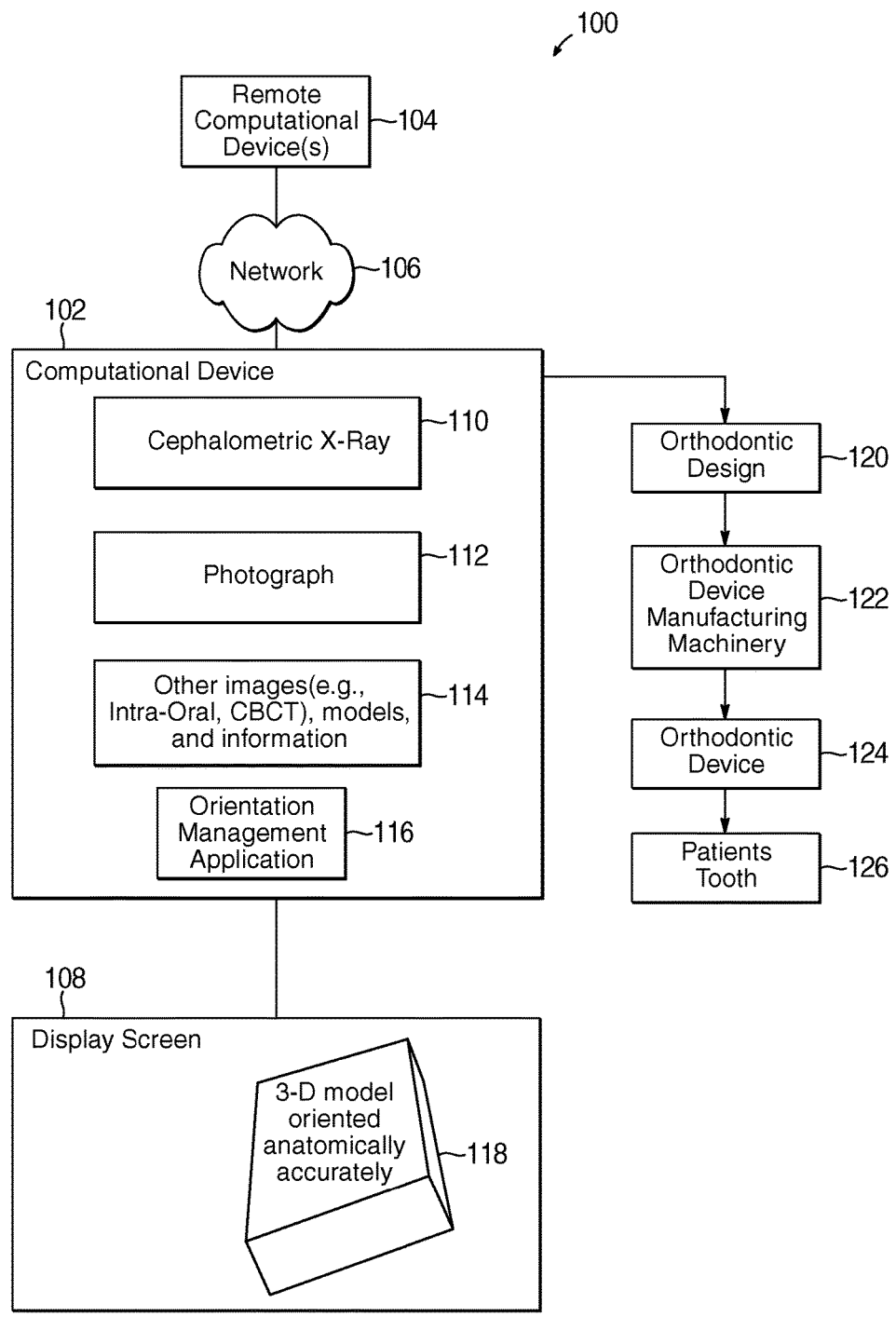
FIG. 1 illustrates a block diagram of computing environment comprising a computational device for orienting three-dimensional models of teeth, in accordance with certain embodiments.

In the following description, reference is made to the accompanying drawings which form a part hereof and which illustrate several embodiments. It is understood that other embodiments may be utilized and structural and operational changes may be made.

Presentation of Three-Dimensional Model of Teeth on Display Screen

While orthodontic diagnosis and treatment planning moved into the digital environment in recent years, one fundamental issue remains unaddressed among software solutions, namely, the precise orientation of the digital teeth model in three-dimensional space. Without this piece of information, the patient's teeth model essentially "floats in space" freely without a proper reference, and clinicians or designers are left to orient it through manual guess work. This leads to inaccuracies in almost all aspects of the treatment planning, including torque computations, the smile arc, axial inclinations, etc.

In currently used virtual interfaces, virtual models of the teeth are displayed, with the occlusal plane parallel to the floor. This results in a significant loss of information about the patient's torque requirements, smile arc, and axial inclinations.

For example, U.S. Pat. No. 8,573,972 describes a method for the automatic construction of occlusal planes. However, its concern is "local", that is, it deals with the relationship between the occlusal plane and individual teeth, rather than the "global" orientation of the occlusal plane in three-dimensional space when the patient's head is perfectly upright. In other words, U.S. Pat. No. 8,573,972 does not discuss information about the occlusal plane in the skeletal context.

Although not stated specifically, U.S. Pat. No. 8,545,221 does indirectly imply the possibility of approximating the occlusal plane orientation through the method of "smile design", by superimposing the "restored smile" over the patient's frontal picture. In particular, if the treatment professional took extra steps to carefully orient the digital teeth model so that it visually matches the patient's teeth in the frontal picture, an approximation to the actual occlusal plane orientation may potentially be achieved. However, it does not appear that this was the intended procedure envisioned by the authors, as U.S. Pat. No. 8,545,221 describes the following: "In various embodiments, the treatment professional can superimpose a number of restored smiles from a smile library database of potential restored smiles to determine the restored smile that is the most appealing to the patient. This can allow the patient to visually see how different smiles would look with their face and/or in their mouth. In some embodiments, a computing device can include executable instructions to guide the treatment professional in placing the restored smile in accordance with established esthetic principles."

Furthermore, even if such steps are taken to approximate the orientation, the outcome is still not acceptable because there is no guarantee that the frontal picture shows the patient's head in a perfectly upright posture, and the fact that the shape-matching procedure is entirely manual, leads to inconsistencies and errors from human factors.

A Frankfort horizontal is a reference plane in orthodontic diagnosis and treatment planning. The Frankfort horizontal is determined by the inferior borders of the bony orbits and the upper margin of the auditory meatus. It passes through the two orbitales and the two tragions and is commonly used as a reference plane in orthodontic diagnosis and treatment planning. The occlusal plane angle of teeth relative to the Frankfort horizontal typically ranges from 2 degrees to 17 degrees, with a mean of about 9 degrees. In currently used virtual interfaces, virtual models of the teeth are displayed, with the occlusal plane parallel to the floor. This results in a significant loss of information about the patient's torque requirements, smile arc, and axial inclinations because for superior results the Frankfort horizontal should be displayed parallel to the floor to the orthodontist or dental practitioner. The Frankfort horizontal may be a reference plane or may be parallel to a reference plane.

Since the occlusal plane is at an angle to the Frankfort horizontal, if the virtual tooth models are displayed with the occlusal plane being parallel to the floor as in currently used visual interfaces, then the torque and other computations for designing braces may be erroneous. It is best for the dental practitioner to look at the virtual model in the same orientation as the orientation in which the proper smile of the patient is achieved. This is achieved when the Frankfort horizontal is parallel to the floor on the display.

Certain embodiments provides mechanisms to orient the virtual teeth model in three-dimensional space. Certain embodiments orient the virtual model of the teeth such that the Frankfort horizontal is displayed along a horizontal plane on the computer screen. It provides insights and information about the patient's occlusal plane in the skeletal context. Subsequent treatment planning decisions regarding torques, smile arc, and axial inclinations, can therefore be made more accurately. In the context of dentistry, anatomical accurate orienting of the three-dimensional model of teeth means that the Frankfort horizontal is displayed along a horizontal plane on the computer screen.

While certain embodiments describe the orienting of three-dimensional models of teeth in three-dimensional space, embodiments are also applicable to other elements of the human anatomy such as ears, nose, eyes, etc., instead of teeth. Additionally, other representations of anatomical features besides the Frankfort horizontal may be used in alternative embodiments. For example, in plastic surgery simulations on a computational device, a three-dimensional model of a nose may be oriented in an anatomically accurate manner in three-dimensional space.

Exemplary Embodiments

FIG. 1 illustrates a block diagram of computing environment 100 comprising a computational device 102 for orienting three-dimensional models of teeth, in accordance with certain embodiments. The computational device 102 is coupled to one or more remote computational devices 104 over a network 106 and is coupled to a display screen [e.g., a liquid crystal display (LCD) or a light emitting diode (LED) display] 108.

The computational device 102 and the remote computational devices 104 may include any suitable computational device such as a personal computer, a server computer, a mini computer, a mainframe computer, a blade computer, a tablet computer, a touchscreen computing device, a telephony device, a cell phone, a mobile computational device, a dental equipment having a processor, etc., and in certain embodiments the computational device 102 may provide web services or cloud computing services. In certain alternative embodiments, more than one computational device may be used for storing data or performing the operations performed by the computational device 102. The network 106 may be a local area network, a wide area network, the Internet, an Intranet or any other type of suitable network.

In certain embodiments, the computational device 102 receives one or more cephalometric X-rays 110 and one or more frontal photographs 112 of a patient from a dental practitioner from one or more the remote computational devices 104 over the network 106. In certain embodiments, the cephalometric x-rays 110 and photographs 112 may be received via mail and stored in a digital form in the computational device 102.

Other images, models, and information 114 may also be stored in the computational device 102. The other images, models, and information 114 may include intra-oral imagery that provides surface data of a patient's crown and CBCT imagery that provides volumetric imagery of a patient's tooth, where the tooth may include both the crown and the root. In alternative embodiments, the surface data of the patient's crown may be provided by imagery that is different from intra-oral imagery, and the volumetric imagery may be provided by other types of tomographic imagery, ultrasonic imagery, magnetic resonance imagery (MRI), etc. Thus the other images, models and information may provide three-dimensional information of the patient's teeth and other structures.

An orientation management application 116 that executes in the computational device 102 uses at the cephalometric X-ray 110, the photograph 112, and optionally the other images, models, and information 114 to achieve anatomically accurate orientation of the digital three-dimensional models 118 (e.g., of the patient's teeth) on the display screen 108, such that dental devices such as braces may be designed properly for the patient. In certain embodiments, the orientation management application 116 may be implemented in software, hardware, firmware or any combination thereof. The three dimensional models 118 may be of other anatomical structures other than teeth, such as ears, nose, eye, heart, lungs, and so on. In dentistry in the anatomically accurate orientation of the three-dimensional model of the teeth, the Frankfort horizontal is a horizontal plane parallel to the floor on which he display screen is placed, where the Frankfort horizontal may or may not be displayed on the display screen.

The dental practitioner uses the computational device 102 and the three-dimensional models 118 to create or generate an orthodontic device design 120. The orthodontic device design 120 is thereafter passed to orthodontic device manufacturing machinery 122 to manufacture an orthodontic device 124 based at least in part on the orthodontic device design 120. The orthodontic device 124 is thereafter applied or coupled to the patients teeth 126 to facilitate the orthodontic work.

Figure 2:
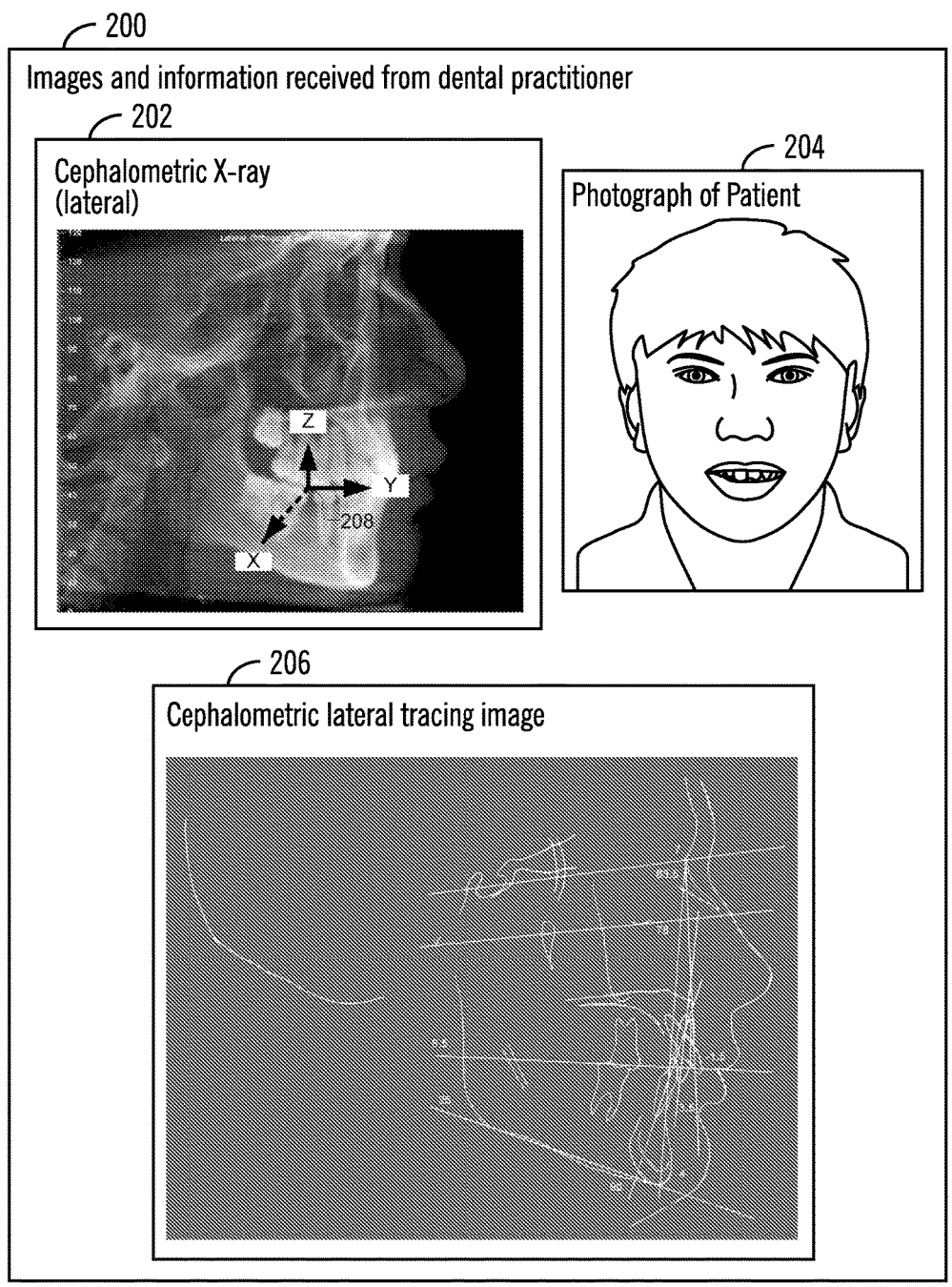
FIG. 2 illustrates a lateral cephalometric X-ray, along with a tracing of important features, and a patient photograph, in accordance with certain embodiments.

FIG. 2 illustrates a block diagram 200 of images and information received from a dental practitioner. The images and information includes at least a lateral cephalometric X-ray 202 of the patient, and the patient's frontal photograph 204. In certain embodiments, the dental practitioner may also sent a cephalometric lateral tracing 206 of features drawn by the dental practitioner based on the cephalometric X-ray 202.

Imposed on the lateral cephalometric X-ray is a coordinate is a coordinate system XYZ 208 with the X-axis projecting out of the paper. Rotations of the head of the patient may occur about any of the X, Y, and Z axis and depending on the rotations of the head of the patient the cephalometric X-ray that is obtained may change.

Figure 3:
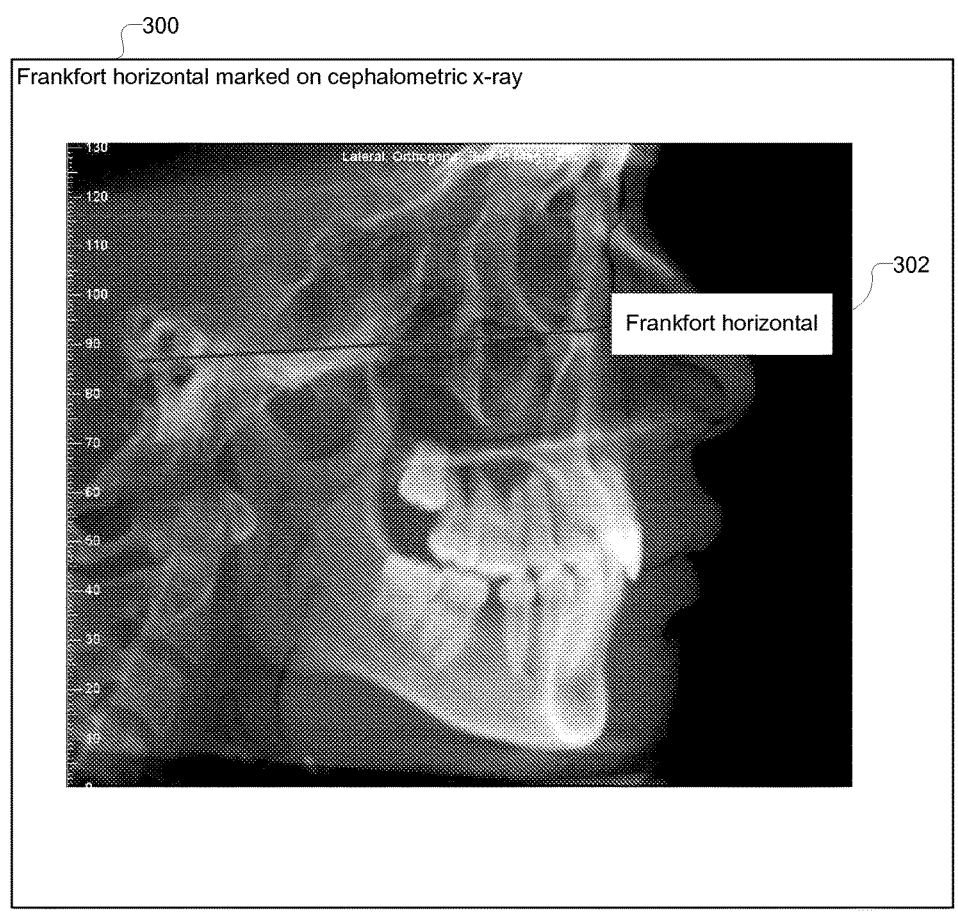
FIG. 3 illustrates a diagram in which the Frankfort horizontal has been marked in the cephalometric X-ray, in accordance with certain embodiments.

FIG. 3 illustrates a block diagram 300 in which the Frankfort horizontal 302 has been marked in the cephalometric X-ray, in accordance with certain embodiments. The Frankfort horizontal 302 is shown as a somewhat inclined line in the lateral cephalometric X-ray. The Frankfort horizontal is not parallel to the floor because while taking the cephalometric X-ray the head of the patient may not have been horizontal.

Figure 4:
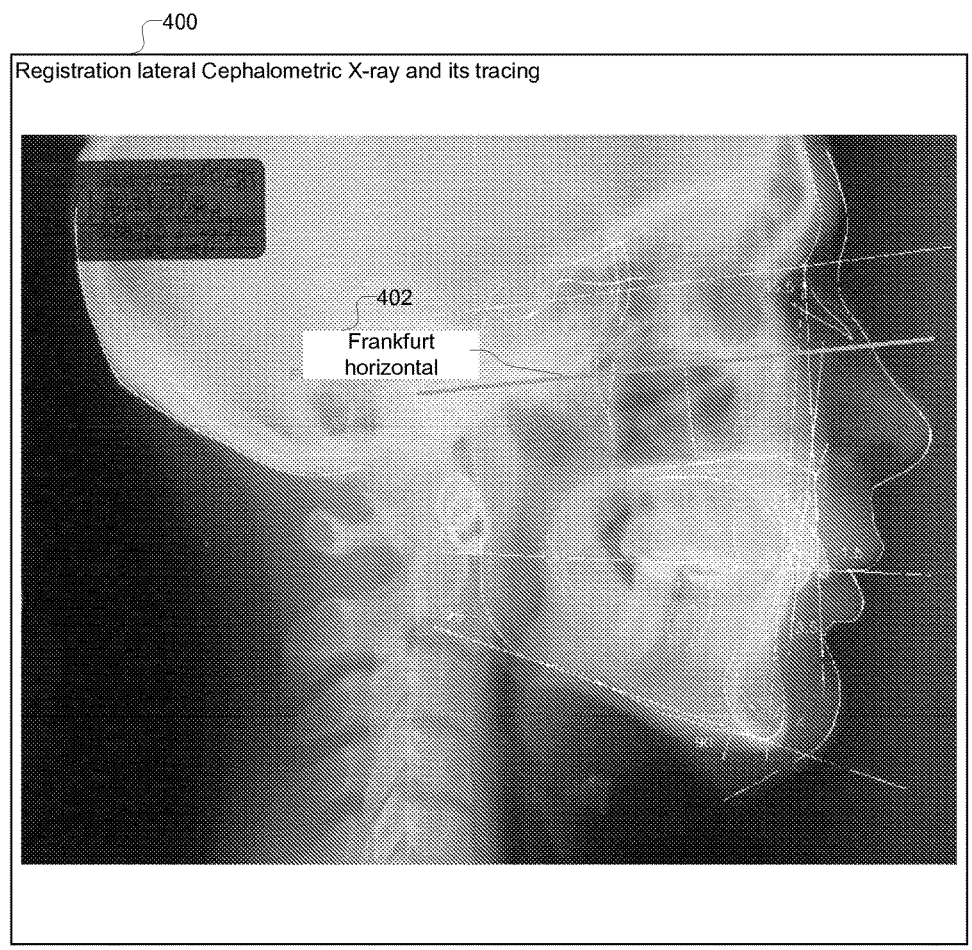
FIG. 4 illustrates a diagram that shows how to register a lateral cephalometric x-ray with its tracing, in accordance with certain embodiments.

FIG. 4 illustrates a block diagram 400 that shows how to register a lateral cephalometric x-ray with its tracing, in accordance with certain embodiments. Known algorithms exist for the registration of the two images, so that they superimpose onto one another as illustrated in FIG. 4. In fact, this registration step may be a pixel-wise superimposition of the cephalometric X-ray 202 and the cephalometric lateral tracing image 206, if one can be certain that the cephalometric lateral tracing image is produced from the cephalometric X-ray image without any distortion (rotation, resizing, cropping, etc.). This eliminates the use of typically computationally-intensive shape matching algorithms.

The feature of interest here is the Frankfort horizontal, which is marked in via the line 402. By definition this represents a horizontal reference for human anatomy. Therefore, if the combined image can be rotated such that the Frankfort horizontal 402 becomes horizontal on the display screen, one can be sure that the teeth in the X-ray image are now representative of their true inclination, when the patient's head is perfectly upright. In this particular example, this requires the combined image to rotate clockwise by just a few degrees.

Figure 5:
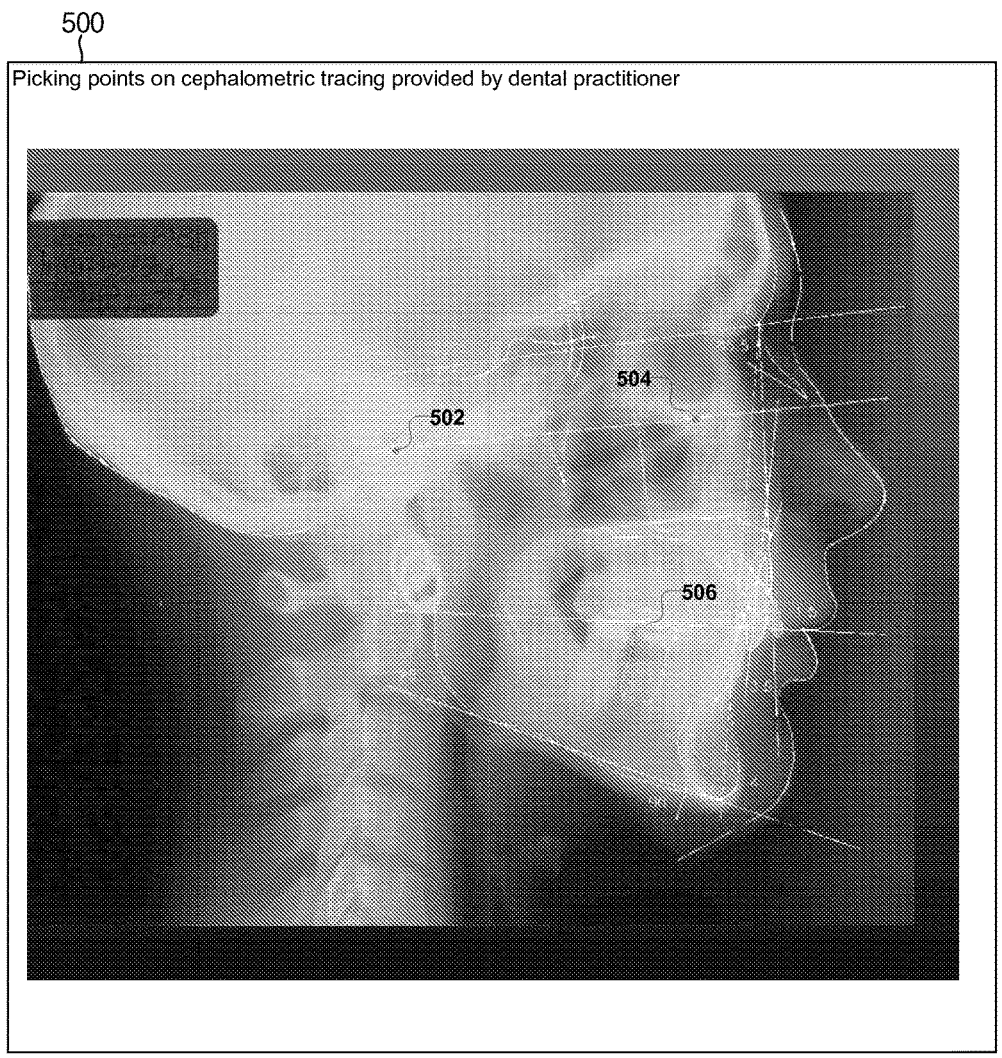
FIG. 5 shows a diagram of mechanisms to pick points on cephalometric tracing to determine the Frankfort horizontal, in accordance with certain embodiments.

Various embodiments may be used to correctly identify the Frankfort horizontal in the combined image. FIG. 5 shows a block diagram 500 of one embodiment, in which the orientation management application 116 may prompt the user to pick two distinct points 502, 504 on the line representing the Frankfort horizontal. Although, human errors are potential risk factors, such errors may be reasonably mitigated with proper training. In FIG. 5 the occlusal plane is shown via reference numeral 506.

Figure 6:
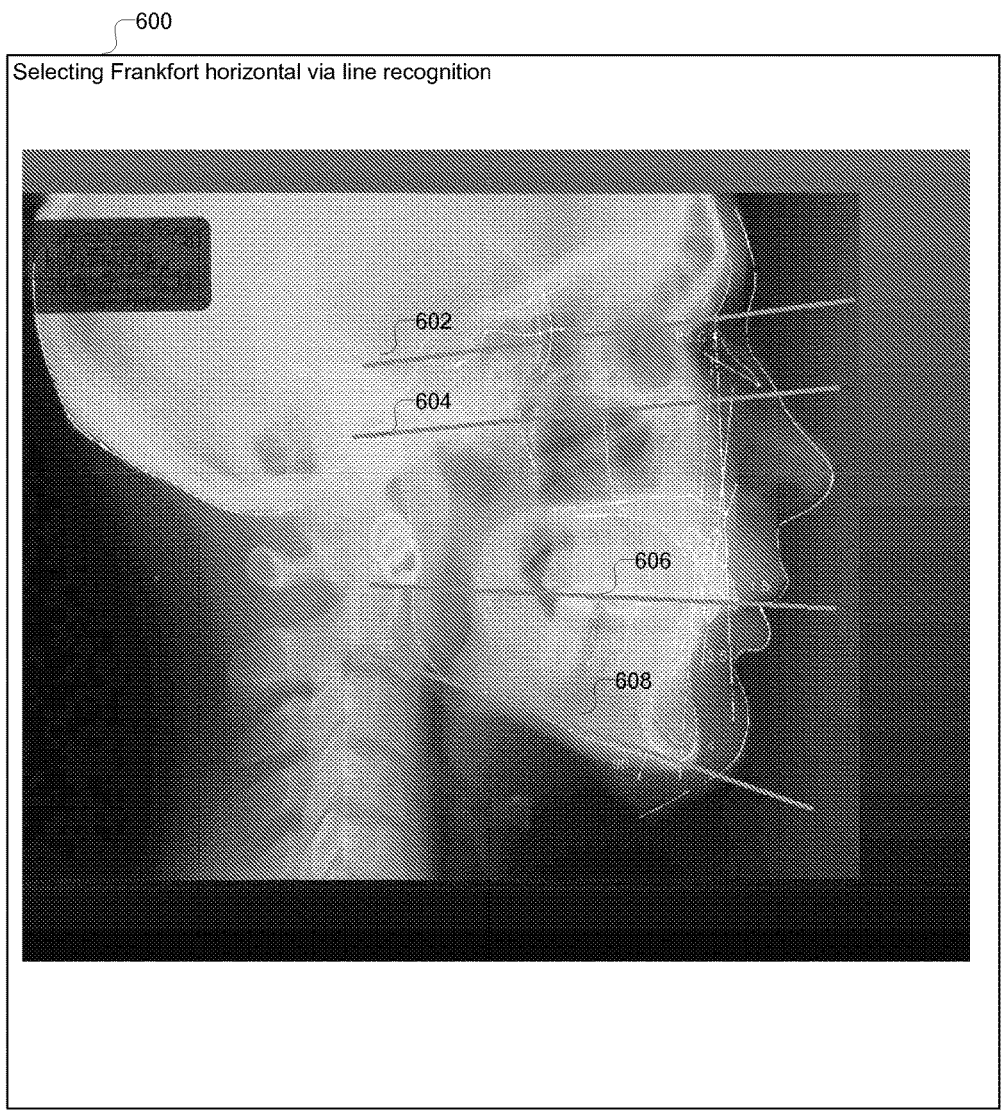
FIG. 6 shows a diagram of mechanisms to determine the Frankfort horizontal via line recognition, in accordance with certain embodiments.

FIG. 6 shows a block diagram 600 of an alternative embodiment in which the orientation management application 116 may employ pattern recognition techniques to identify roughly left-to-right straight lines 602, 604, 606, 608 in the cephalometric image, and present them as selectable objects on screen. The user may then select the appropriate line to correspond to the Frankfort horizontal. This is relatively more complicated in comparison to the point picking mechanism shown in FIG. 5, with the advantage that potential errors in point picking is now eliminated. Errors in wrong line selection can still happen, which again can be reasonably mitigated with proper training.

Figure 7:
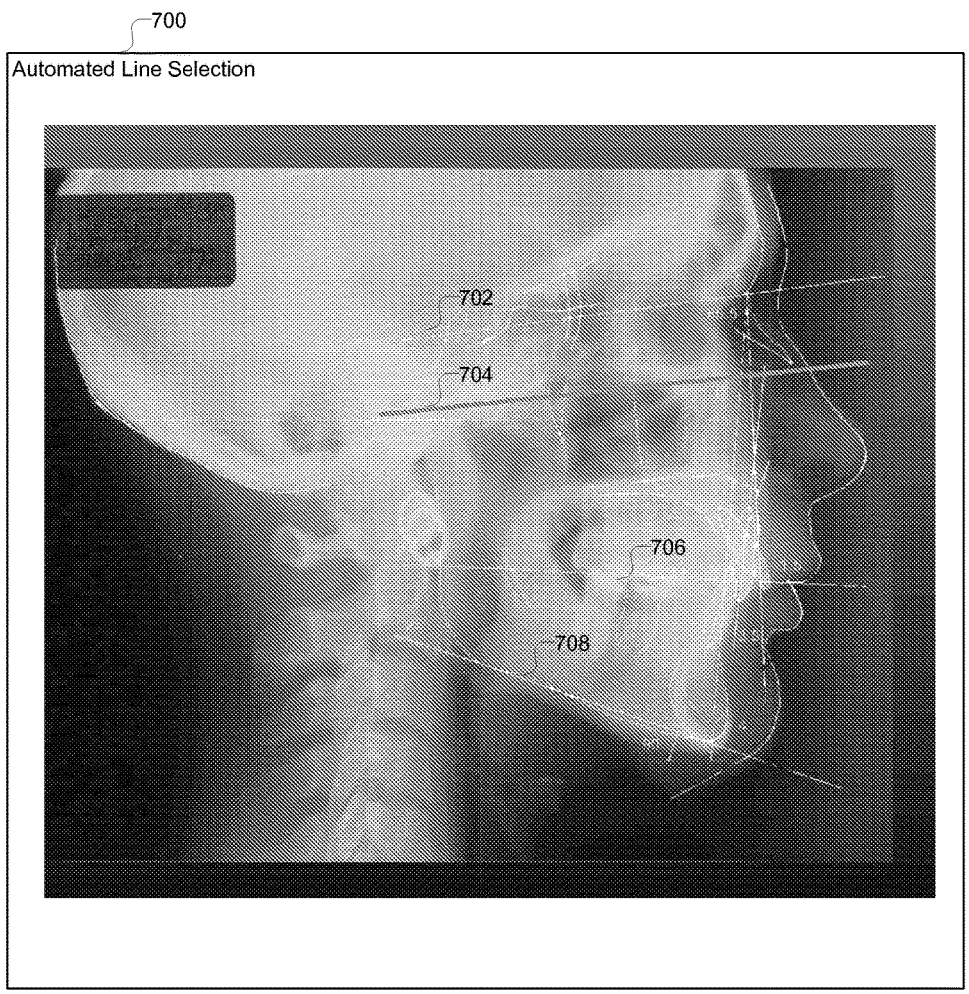
FIG. 7 shows a diagram of mechanisms to determine the Frankfort horizontal via automated line selection, in accordance with certain embodiments.

FIG. 7 shows a block diagram 700 of a fully automated approach for selecting the Frankfort horizontal. Such an approach is possible, if it can be guaranteed that there will always be a fixed number (e.g. four 702, 704, 706, 708) of roughly left-to-right straight lines in any tracing image generated form lateral cephalometric X-rays, and the Frankfort horizontal will always be a certain one (say, the second 704) from the top. The system can then identify all of these lines, and simply choose the right one automatically. This eliminates potential human errors completely, while uncertainty exists as to whether the assumption about these lines is always valid.

Certain embodiments achieve precise determination of the occlusal plane orientation by first determining a proper placement of the cephalometric X-ray image on screen, so that a horizontal Frankfort horizontal reference is established. Then a determination is made of a proper placement of the teeth model in three-dimensional space, so that matching of the silhouettes of the visible teeth and the teeth in the cephalometric X-ray image is established.

Figure 8:
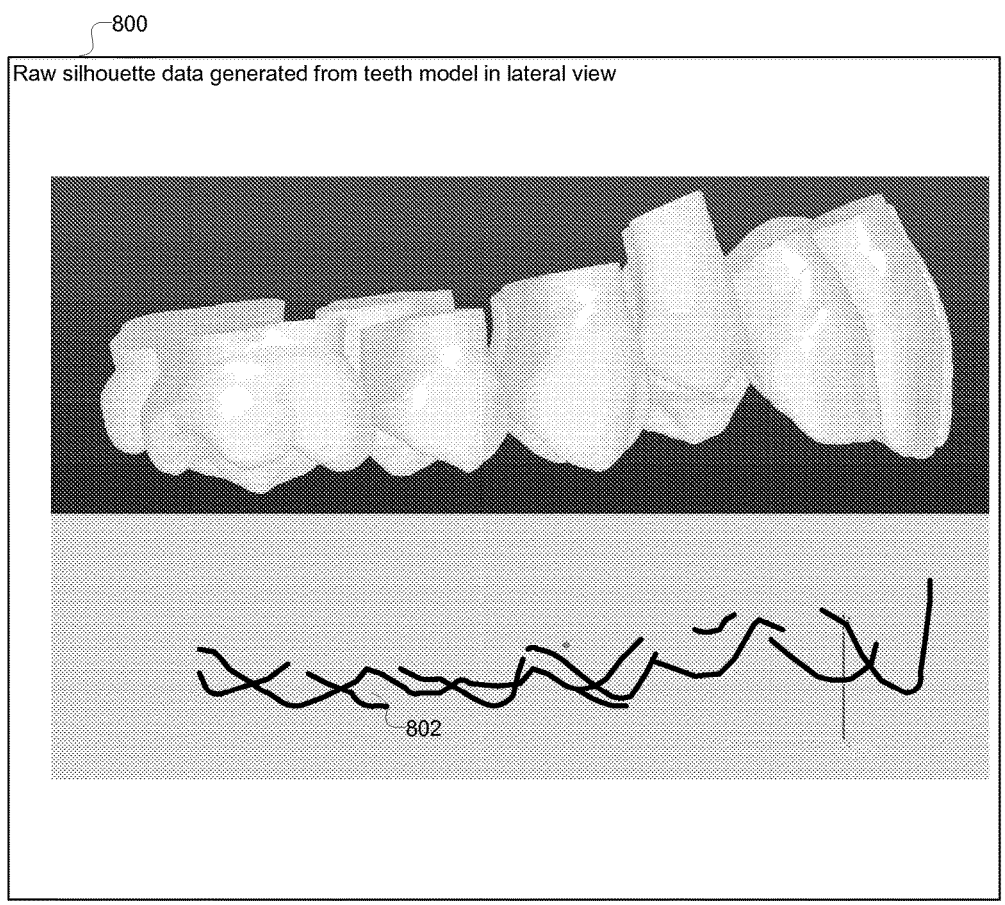
FIG. 8 illustrates a diagram that shows raw silhouette data generated from teeth model in lateral view, in accordance with certain embodiments.

With the proper on-screen placement of the lateral cephalometric X-ray image established, the next operation is to find a proper three-dimensional placement of the teeth model, using the X-ray image as a reference. This can be achieved by identifying and matching the silhouettes (in lateral view) of both the teeth model, and the teeth in the X-ray image as shown in block diagram 800 of FIG. 8. Here we define the silhouette of teeth in a certain view to be the envelope of all incisal/buccal edges visible in that view. Standard scanline rendering techniques in computer graphics can be easily adapted to generate raw silhouette data for the teeth model as shown in FIG. 8 via reference numeral 802.

Figure 9:
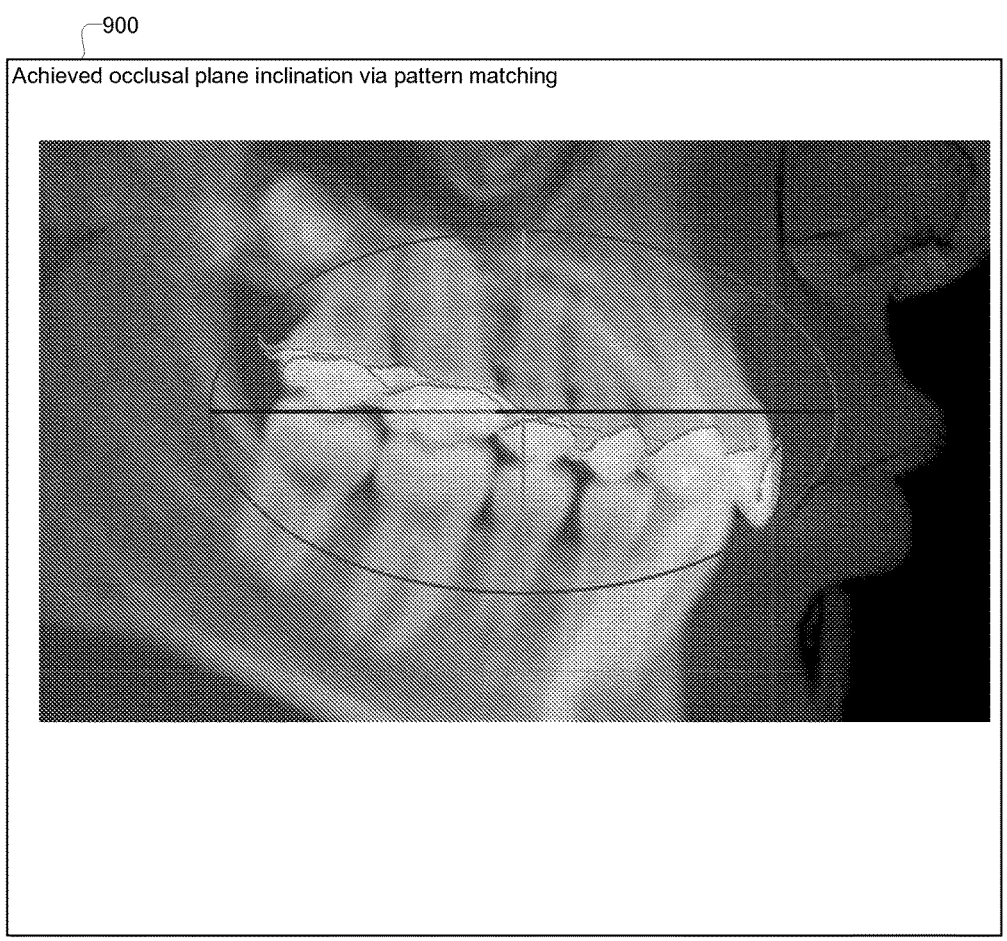
FIG. 9 illustrates a diagram that shows the achieved occlusal plane inclination via pattern matching, in accordance with certain embodiments.

Given the silhouette of the teeth model, which represents the target shape that should also be present in the X-ray image, the problem now becomes one of pattern matching. Certain embodiments employ well-known algorithms such as the Sobel operator to accentuate all edges in the X-ray image. Generalized Hough Transform (GHT) may then be applied to identify the target shape from all of these candidate edges. The output of GHT provides information not only the relative positioning between the X-ray image and the teeth model, but relative scaling and rotation as well. FIG. 9 illustrates the achieved outcome in block diagram 900. In FIG. 9 the X-ray image is scaled and positioned to match the silhouette of the (maxillary) teeth model, and the teeth model is rotated (clockwise) to match the silhouette of the X-ray teeth image. Expected occlusal plane inclination angle is now established.

Notice that in addition to the inclination, or torque, degree of freedom, that is being automatically adjusted by the orientation management application, the teeth model can also transform rotationally in two other degrees of freedom: tip, which rocks the teeth occlusal-gingivally, and rotation, which rotates the entire arch mesial-distally. For ease of understanding, the disclosure uses rotations with respect to the X, Y, and Z axis as shown in FIG. 2, block 208. Although probably minor in most patient cases, discrepancies in these degrees of freedom do affect the shape of the silhouette collected, and as a result degrade the accuracy of pattern matching. This problem can be addressed by performing the pattern matching algorithms repeatedly in a certain sample space of the two degrees of freedom. For example, if the user discretizes between −10 to +10 degrees of rotational transformation for both degrees of freedom, the operation tries out all of the 21 times 21 scenarios, and picks the one that produces the best match.

Figure 10:
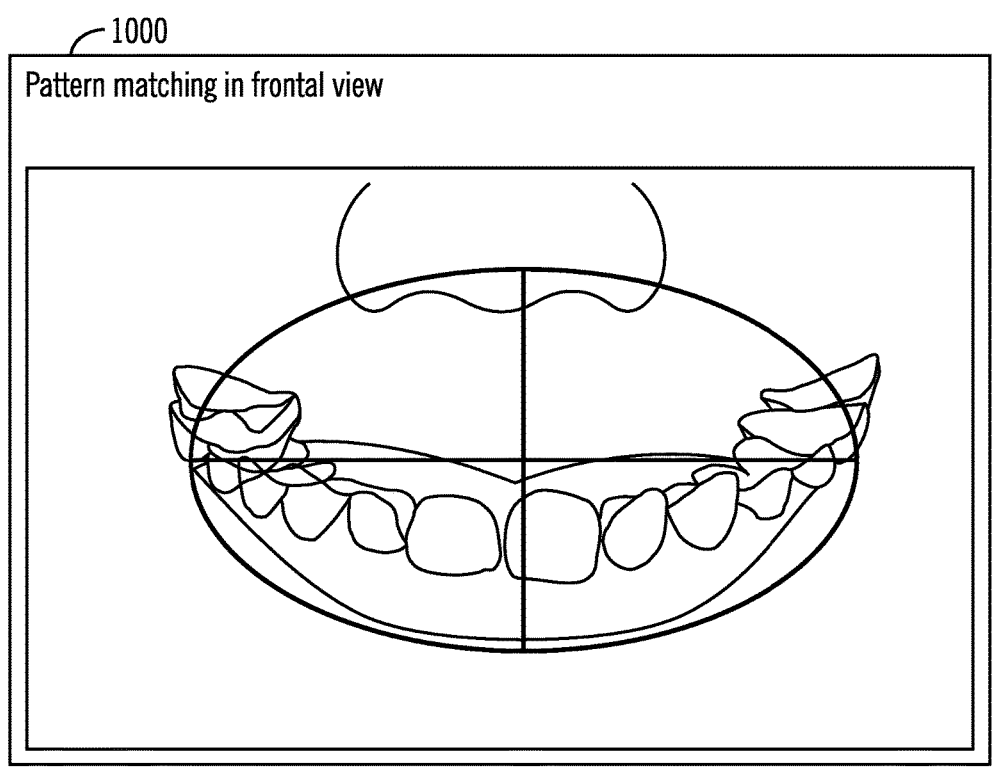
FIG. 10 illustrates a diagram that shows pattern matching in frontal view, in accordance with certain embodiments.

A much better alternative is to obtain insights about these other degrees of freedom by looking at the teeth model from a different view. FIG. 10 in block diagram 1000 shows the same pattern matching mechanism applied to the same patient case, using the frontal smiling picture as the reference. If required, the system can alternate between these two views repeatedly until the total error in pattern matching is minimized. In practice, since the user is principally concerned with the accuracy of the inclination angle, one run in each view with some manual fine-tuning from the user should suffice.

Therefore, certain embodiments answers the question of how one orients the teeth model in three-dimensional space. It provides insights and information about the patient's occlusal plane in the skeletal context. Subsequent treatment planning decisions such as torques, smile arc, and axial inclinations, can now be made with greater accuracy. The orientation of the teeth model in three-dimensional space is determined more accurately.

Figure 11:
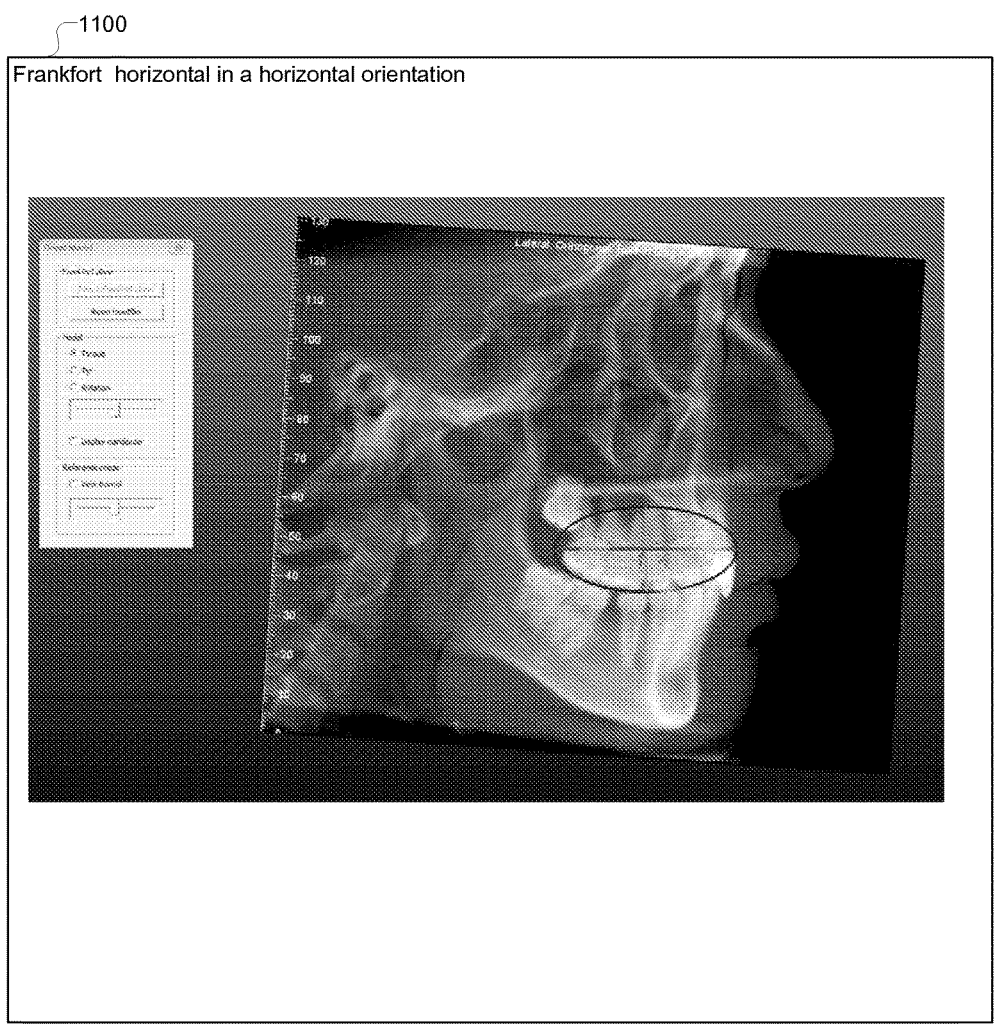
FIG. 11 illustrates a diagram that shows the Frankfort horizontal in a horizontal orientation, in accordance with certain embodiments.

FIG. 11 illustrates a diagram 1100 that shows the Frankfort horizontal in a horizontal orientation, in accordance with certain embodiments. It can be seen that the three-dimensional tooth model is being oriented after the Frankfort horizontal is in a horizontal orientation.

Figure 12:
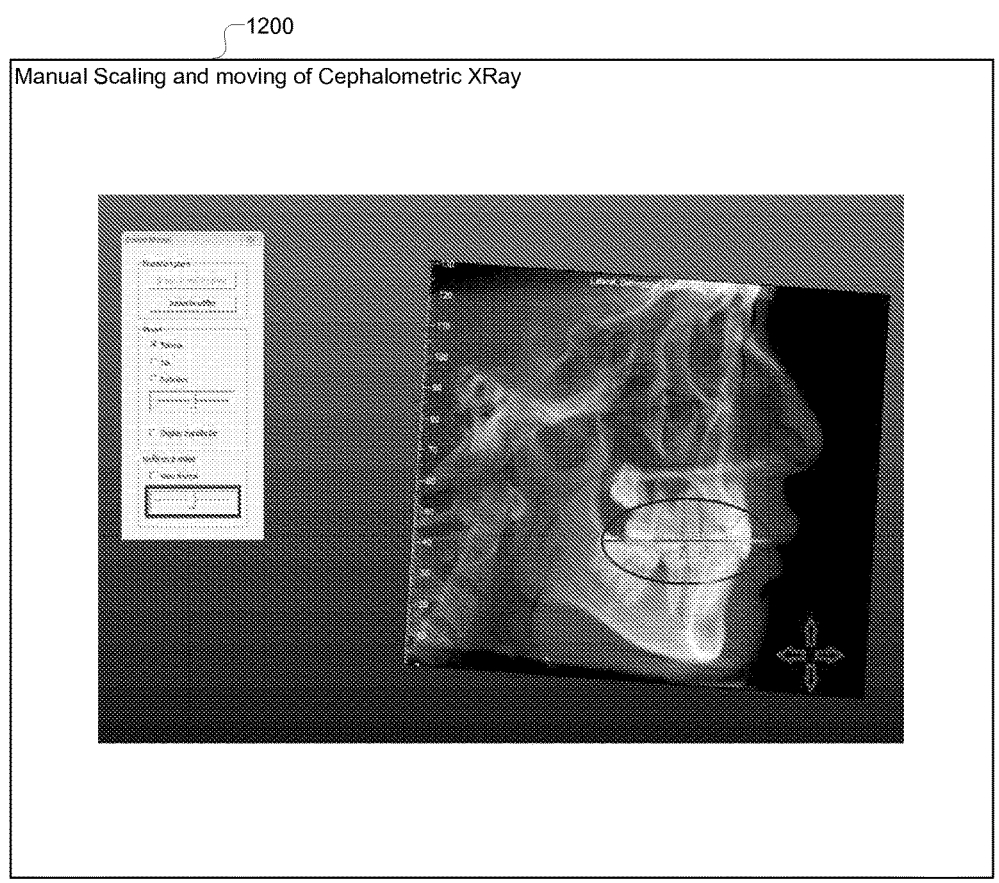
FIG. 12 illustrates a diagram that shows manual scaling and moving of the cephalometric X-ray, in accordance with certain embodiments.

FIG. 12 illustrates a diagram 1200 that shows manual scaling and moving of the cephalometric X-ray to match the three-dimensional tooth model, in accordance with certain embodiments. The scaling is needed as the cephalometric X-ray may be in different units than the three-dimensional tooth models. The background image is the cephalometric X-ray image and it can be scaled and moved, whereas the three-dimensional tooth model may be rotated but should not be scaled.

Figure 13:
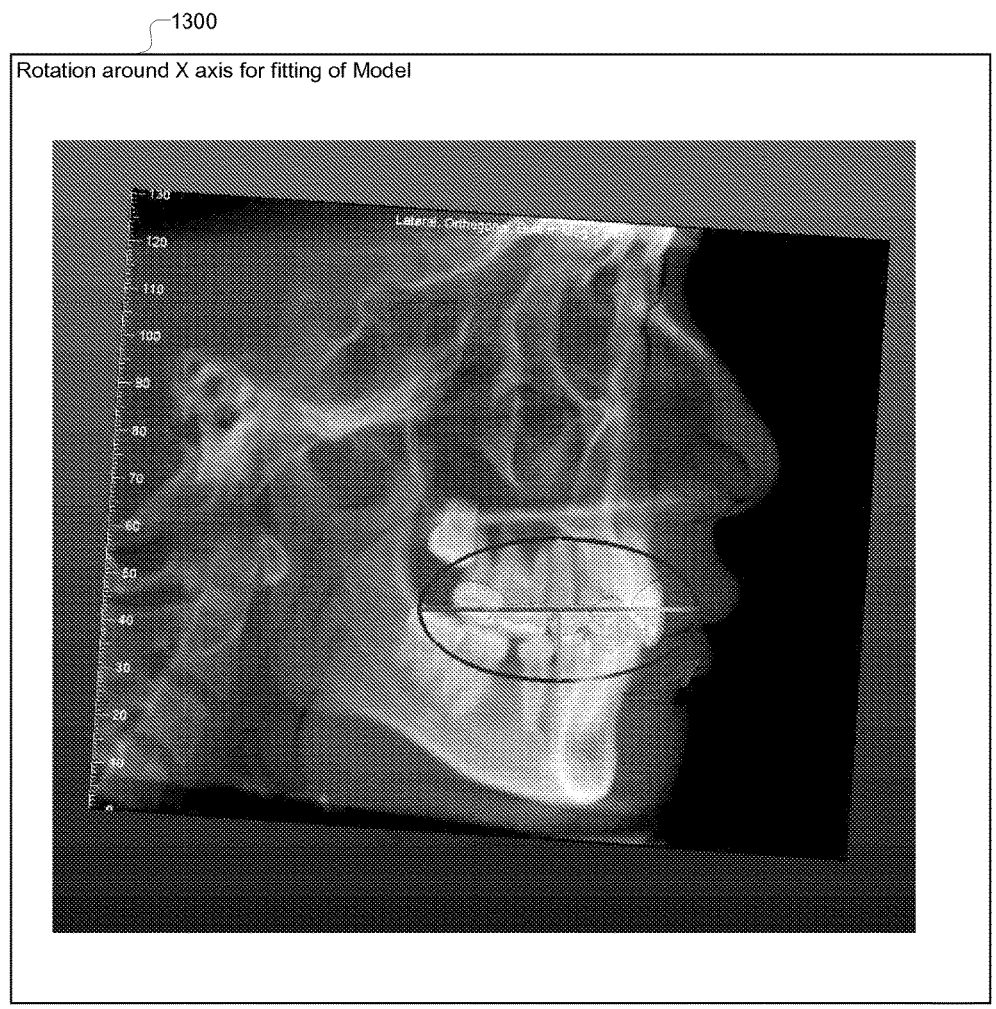
FIG. 13 illustrates a diagram that shows the manual rotational adjustment of the model with respect to X-axis of the model, in accordance with certain embodiments.
Figure 14:
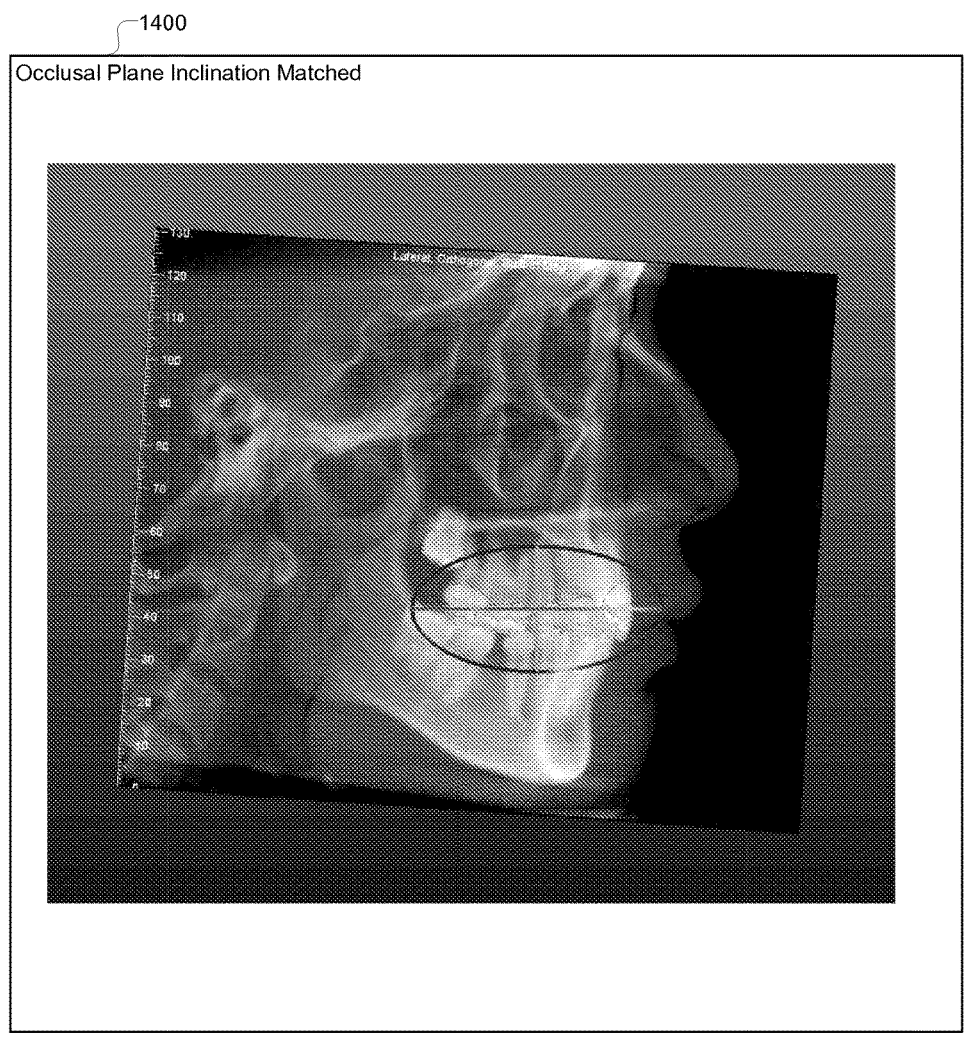
FIG. 14 illustrates a diagram that shows the matching of the occlusal plane inclination, in accordance with certain embodiments.

FIG. 13 illustrates a diagram 1300 that shows the rotation around the X-axis for proper fitting of the tooth model to the cephalometric image, in accordance with certain embodiments. FIG. 14 illustrates a diagram 1400 that shows the matching of the occlusal plane inclination, in accordance with certain embodiments.

Figure 15:
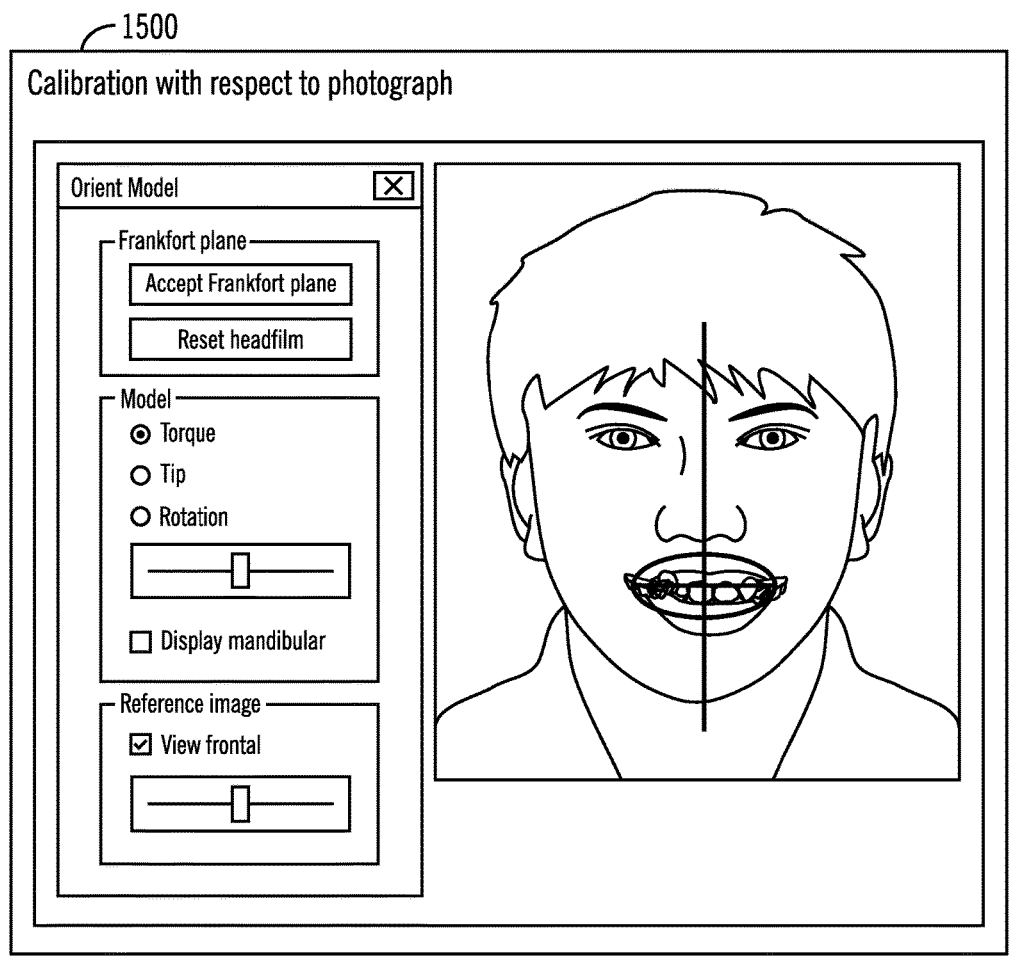
FIG. 15 illustrates a diagram that shows a calibration with respect to a frontal photograph, in accordance with certain embodiments.
Figure 16:
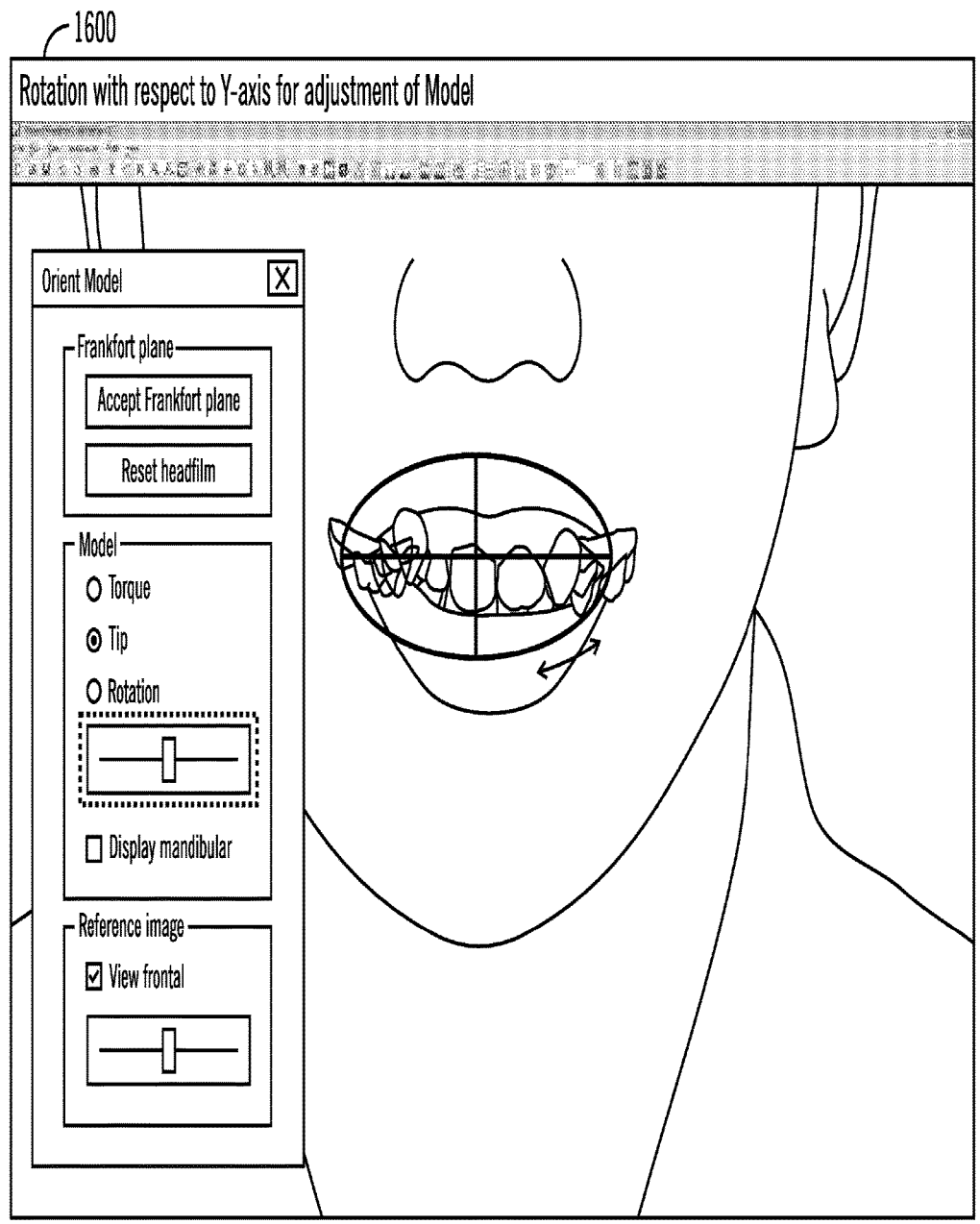
FIG. 16 illustrates a diagram that shows manual rotational adjustment with respect to Y-axis of the model, in accordance with certain embodiments.
Figure 17:
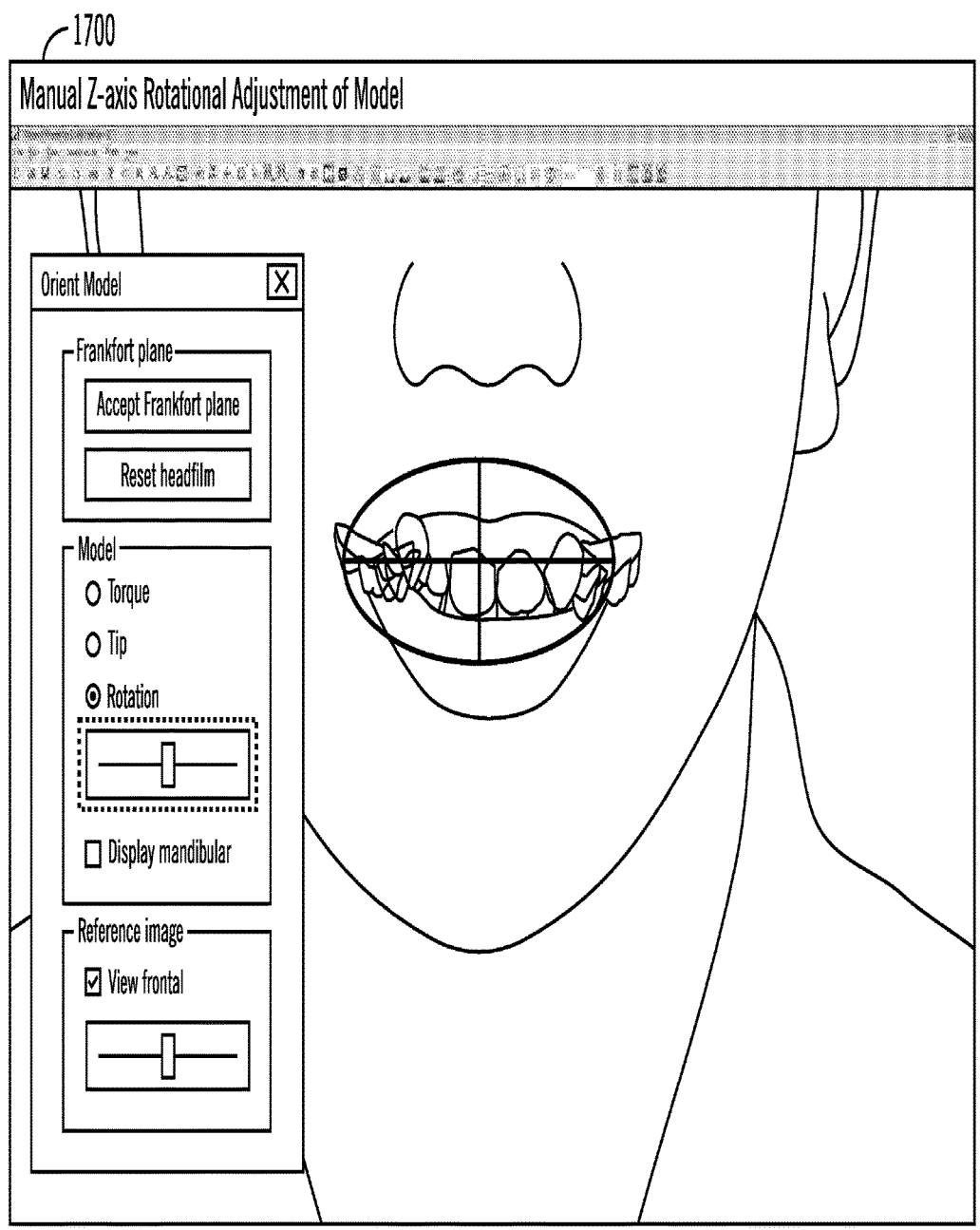
FIG. 17 illustrates a diagram that shows manual rotational adjustment of the model with respect to Z-axis, in accordance with certain embodiments.
Figure 18:
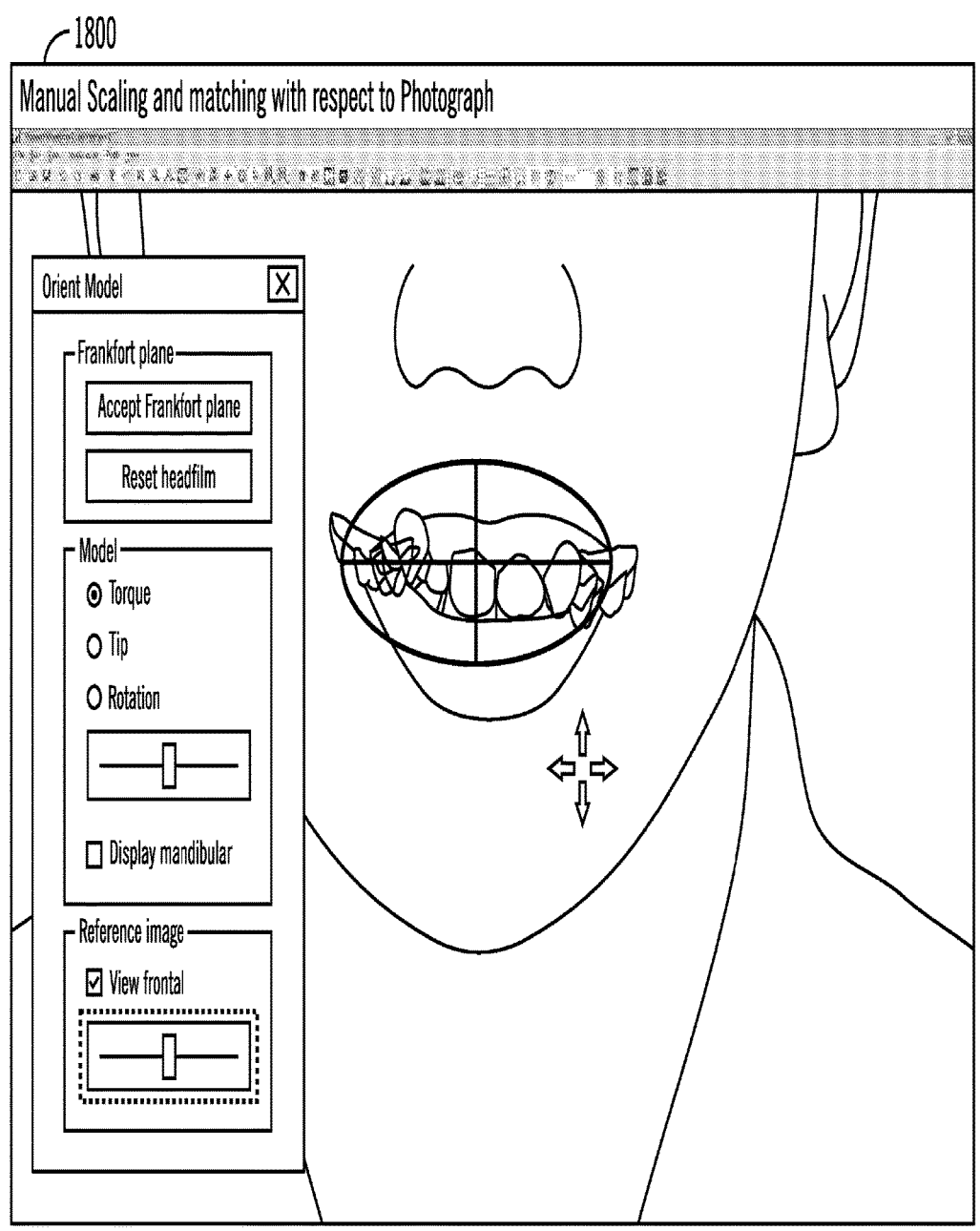
FIG. 18 illustrates a diagram that shows manual scaling and matching with respect to a photograph, in accordance with certain embodiments.

FIG. 15 illustrates a diagram 1500 that shows a calibration with respect to a frontal photograph, in accordance with certain embodiments. Such calibration of the three-dimensional tooth model with respect to a fontal photograph of the patient may improve the accuracy of orientation of the three-dimensional tooth model in space. FIG. 16 illustrates a diagram 1600 that shows manual rotations around Y-axis to adjust the model with respect to the frontal photograph, in accordance with certain embodiments. FIG. 17 illustrates a diagram 1700 that shows manual rotational adjustment of the model around the Z-axis with respect to the frontal photograph, in accordance with certain embodiments. FIG. 18 illustrates a diagram 1800 that shows manual scaling and matching of the model with respect to a photograph, in accordance with certain embodiments. The operations shown in FIGS. 15-18 further refine and the orientation of the three-dimensional model in space.

Figure 19:
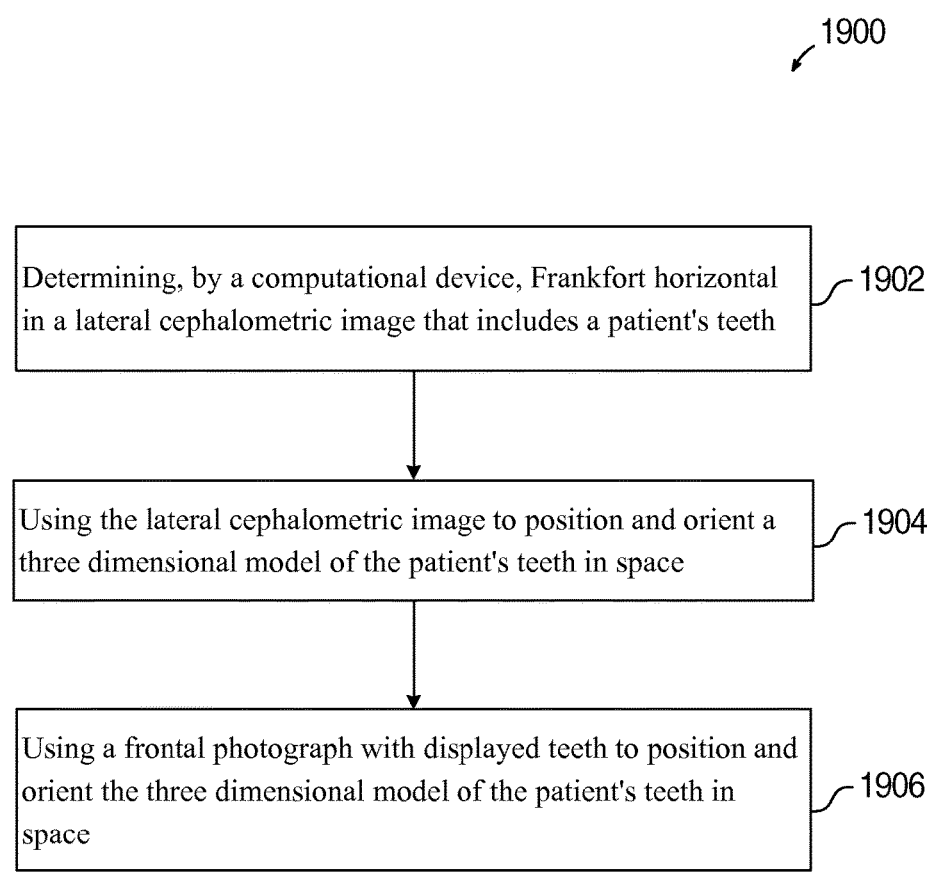
FIG. 19 illustrates operations for orienting three-dimensional tooth models in space, in accordance with certain embodiments.

FIG. 19 illustrates a flowchart 1900 that shows operations for orienting three-dimensional tooth models in space, in accordance with certain embodiments. The operations shown in FIG. 19 may be performed by the orientation management application 116 that executes in the computational device 102.

Control starts at block 1902 in which determination is made of a horizontal Frankfort horizontal in a lateral cephalometric image that includes a patient's teeth. The lateral cephalometric image is used (at block 1904) to orient a three-dimensional model of the patient's teeth in space. Control proceeds to block 1906 in which a frontal photograph with displayed teeth is used to orient the three-dimensional model of the patient's teeth in space.

Figure 20:
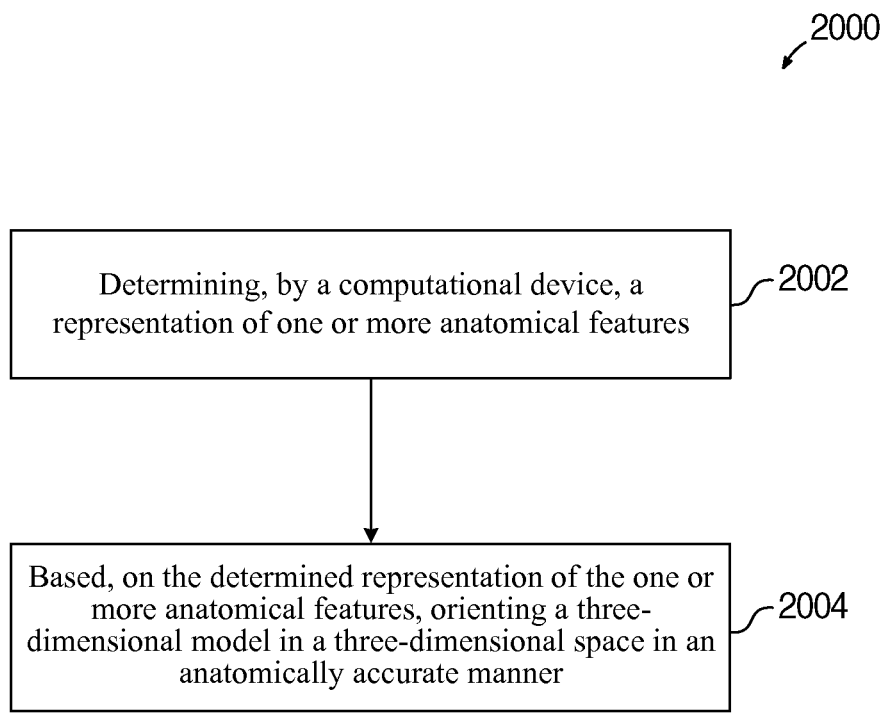
FIG. 20 illustrates operations for orienting three-dimensional models in space, in accordance with certain embodiments.

FIG. 20 illustrates a flowchart 2000 that shows operations for orienting three-dimensional models in space, in accordance with certain embodiments. The operations shown in FIG. 20 may be performed by the orientation management application 116 that executes in the computational device 102.

Control starts at block 2002 in which a computational device determines a representation of one or more anatomical features. The determined representation may be a Frankfort horizontal or some other element (e.g. a plane that is parallel to the Frankfort plane or some other representation) in dentistry or in other arts, such as plastic surgery, automated surgery, etc. In certain embodiments, the Frankfort horizontal is in a fixed relationship with an occlusal plane of the teeth.

Control proceeds to block 2004 in which based on the determined representation of the one or more anatomical features, a three-dimensional model is oriented in a three-dimensional space in an anatomically accurate manner. In dentistry, the three-dimensional model may be a model of teeth. In other arts, the three-dimensional model may be a model of some other anatomical element such as a nose, a heart, a lung, etc.

Therefore, FIGS. 1-20 illustrate various embodiments to orient the three-dimensional model of a patients's teeth (or other anatomical features) in space when displayed on a display screen. The physical relationship between the Frankfort horizontal and the occlusal plane is used in various embodiments to orient the three-dimensional model of a patients's teeth in space. Aligners and braces designed and constructed based on proper positioning and orienting of the three-dimensional model of a patients's teeth in space are superior to aligners and braces designed and constructed without proper positioning and orienting of the three-dimensional model of a patients's teeth in space. The digital models of other anatomical features may also be oriented in space in accordance with certain described embodiments.

Additional Details of Embodiments

The operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal with computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 21:
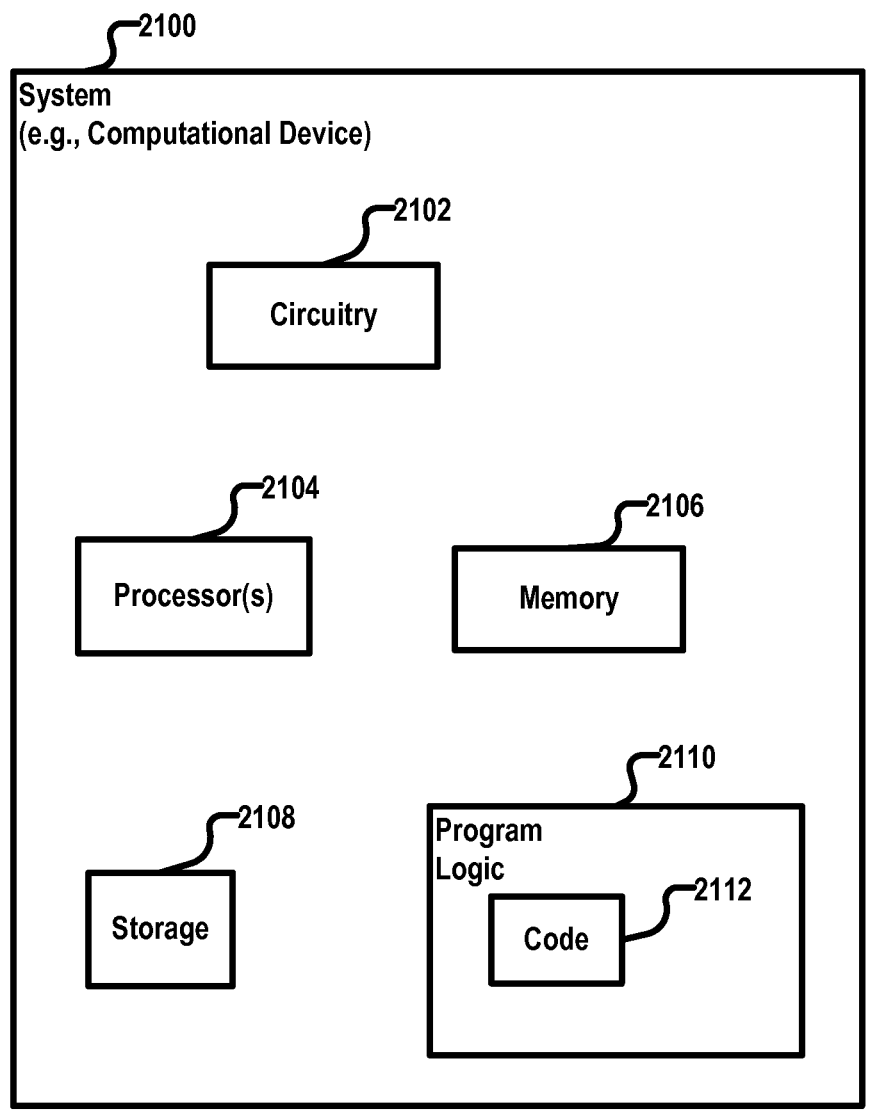
FIG. 21 illustrates a block diagram of computational device, in accordance with certain embodiments.

FIG. 21 illustrates a block diagram that shows certain elements that may be included in the computational device 102 in accordance with certain embodiments. The system 2100 may comprise the computational device 102, 2502 and may include a circuitry 2102 that may in certain embodiments include at least a processor 2104. The system 2100 may also include a memory 2106 (e.g., a volatile memory device), and storage 2108. The storage 2108 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 2108 may comprise an internal storage device, an attached storage device and/or a network accessible storage device. The system 2100 may include a program logic 2110 including code 2112 that may be loaded into the memory 2106 and executed by the processor 2104 or circuitry 2102. In certain embodiments, the program logic 2110 including code 2112 may be stored in the storage 2108. In certain other embodiments, the program logic 2110 may be implemented in the circuitry 2102. Therefore, while FIG. 21 shows the program logic 2110 separately from the other elements, the program logic 2110 may be implemented in the memory 2106 and/or the circuitry 2102.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of manufacturing an orthodontic aligner or an orthodontic brace for a patient, the method comprising:
    determining, by a computational device, a representation of one or more anatomical features in an image that includes the patient's teeth;
    overlapping the image and a three-dimensional model of the patient's teeth in a three-dimensional space;
    correcting in an anatomically accurate manner, based at least in part on the determined representation of the one or more anatomical features, the orientation by which the three-dimensional model is viewed in the three-dimensional space;
    after correcting the orientation, measuring an orientation of an occlusal plane of the patient's teeth relative to the determined representation in the three-dimensional space;
    using the measured orientation to create a digital design for an orthodontic aligner or an orthodontic brace; and
    manufacturing the orthodontic aligner or the orthodontic brace based on the digital design.

2. The method of claim 1, wherein the representation of the one or more anatomical features comprises a Frankfort horizontal.

3. The method of claim 2, wherein the Frankfort horizontal is in a fixed relationship with the occlusal plane of the teeth and is parallel to a reference plane.

4. The method of claim 3, wherein the image includes a lateral cephalometric image and the reference plane is parallel to a floor, the method further comprising:
    determining a horizontal line corresponding to the Frankfort horizontal in the lateral cephalometric image; and
    wherein correcting the orientation by which the three-dimensional model is viewed includes aligning the teeth in the lateral cephalometric image with the teeth in the three-dimensional model in the three-dimensional space.

5. The method of claim 4, wherein aligning includes identifying and matching a silhouette of the teeth in the three-dimensional model and the teeth in the lateral cephalometric image.

6. The method of claim 5, wherein the silhouette of the teeth comprises an envelope of all incisal and buccal edges of teeth that are visible.

7. The method of claim 6, wherein matching includes rotating the three-dimensional model to match the silhouette of the teeth in the three-dimensional model and the teeth in the lateral cephalometric image.

8. The method of claim 4, wherein determining the horizontal line corresponding to the Frankfort horizontal further comprises determining at least two different points on a line representing the Frankfort horizontal.

9. The method of claim 4, wherein determining the horizontal line corresponding to the Frankfort horizontal further comprises:
    identifying and displaying left to right straight lines in a cephalometric tracing of the cephalometric image; and
    determining which of the displayed left to right straight lines has been selected by a user as a line corresponding to the Frankfort horizontal.

10. The method of claim 4, the method further comprising:
    identifying left to right straight lines in a cephalometric tracing of the cephalometric image; and
    determining which of the left to right straight lines corresponds to the Frankfort horizontal.

11. The method of claim 4, the method further comprising:
    using a frontal photograph with displayed teeth to orient the three-dimensional model in the three-dimensional space.

12. The method of claim 4, wherein correcting includes rotating the three-dimensional model in three-dimensional space to orient the three-dimensional model in the three-dimensional space relative to the lateral cephalometric image.

13. The method of claim 4, wherein graphical user interface controls are used to position and orient the three-dimensional model in the three-dimensional space.

14. The method of claim 1, wherein the measured orientation is an angle between the occlusal plane and the representation.

15. The method of claim 14, wherein the representation is a Frankfort horizontal and the image is a lateral image and wherein measuring the angle is accomplished in the lateral image in the three-dimensional space.

16. The method of claim 14, wherein the image is a lateral cephalometric image and wherein measuring the angle is accomplished in the lateral cephalometric image in the three-dimensional space.

17. The method of claim 1, wherein after correcting and before measuring, the method further comprises:
    overlapping the oriented three-dimensional model and a second image that includes the patient's teeth different from the image in the three-dimensional space, and
    reorienting the three-dimensional model relative to the patient's teeth in the second image.

18. The method of claim 17, wherein prior to measuring, the method further comprises:
    repeating one or more times, orienting the oriented three-dimensional model relative to the image in the three-dimensional space and orienting the oriented three-dimensional model relative to the second image in the three-dimensional space to reduce an error between the three-dimensional model and each image to below a threshold value.

19. The method of claim 17, wherein the image is a lateral cephalometric image and the second image is a frontal photograph of the patient.

* * * * *